United States Patent [19]
Bonnem et al.

[11] Patent Number: 5,679,356
[45] Date of Patent: Oct. 21, 1997

[54] USE OF GM-CSF AS A VACCINE ADJUVANT

[75] Inventors: Eric M. Bonnem, Mr. Vernon, N.H.; Imtiaz A. Chaudry, North Caldwell; Elliot Stupak, West Caldwell, both of N.J.

[73] Assignee: Schering Corporation, Kenilworth, N.J.

[21] Appl. No.: 367,114

[22] PCT Filed: Jul. 7, 1993

[86] PCT No.: PCT/US93/06298

§ 371 Date: Jan. 5, 1995

§ 102(e) Date: Jan. 5, 1995

[87] PCT Pub. No.: WO94/01133

PCT Pub. Date: Jan. 20, 1994

Related U.S. Application Data

[63] Continuation-in-part of Ser. No. 910,399, Jul. 8, 1992, abandoned.

[51] Int. Cl.⁶ ............ A61K 38/19; A61K 39/145; A61K 39/29; A61K 45/00

[52] U.S. Cl. ............ 424/278.1; 424/209.1; 424/227.1

[58] Field of Search ............ 424/278.1, 195.11, 424/227.1, 209.1

[56] References Cited

U.S. PATENT DOCUMENTS 5,100,664 3/1992 Doyle et al. ............ 424/92

FOREIGN PATENT DOCUMENTS

91/01146 2/1991 WIPO ............ A61K 47/48

OTHER PUBLICATIONS

Morrissey et al., Journal of immunology, vol. 139 issue 4, pp. 1113–1119. "Granulocyte–macrophage colony–stimulating factor augments the primary antibody response by enhancing the function of antigen–presenting cells, " Aug. 15, 1987.

Schrader, 1991, *Molecular Immunology* 28 (3):295–299.

Patent abstracts of Japan, 1988, vol. 12 No. 30: (C485) (2950).

*Primary Examiner*—Robert D. Budens
*Attorney, Agent, or Firm*—Norman C. Dulak; Cynthia L. Foulke

[57] ABSTRACT

The present invention is a method for enhancing the immune response of a mammal to a vaccine by administering to such a mammal an effective amount of GM-CSF in conjunction with a vaccine. The present invention further provides for pharmaceutical compositions containing an effective amount of GM-CSF and a vaccine. Kits containing GM-CSF and a vaccine are also disclosed.

10 Claims, No Drawings

USE OF GM-CSF AS A VACCINE ADJUVANT

This is a U.S. national application corresponding to International Application No. PCT/US93/06298, filed Jul. 7, 1993 designating the U.S., which PCT application is a continuation-in-part of U.S. application Ser. No. 07/910,399, filed Jul. 8, 1992, now abandoned.

FIELD OF THE INVENTION

The present invention relates to the use of granulocyte-macrophage-colony stimulating factor (GM-CSF), particularly human GM-CSF, as a vaccine adjuvant.

BACKGROUND OF THE INVENTION

Active immunization is the administration of an antigen to an animal to bring about an immune response in the animal. A vaccine against a microorganism is an antigenic preparation which when inoculated into a non-immune individual will confer active immunity to the microorganism but will not cause disease. Specificity and memory, the two key elements of the adaptive immune system, are exploited in vaccination, since the adaptive immune system mounts a much stronger response on second encounter with an antigen. This secondary immune response is both faster to appear and more effective than the primary response. The principle of vaccine development is to alter a microorganism or its toxins (natural antigens) in such a way that they become innocuous without losing antigenicity. Alternatively, antigenic polypeptides of the organism in question can be produced by recombinant methods or by synthetic chemistry to produce an effective vaccine.

One problem that frequently is encountered in the course of active immunization is that the antigens used in the vaccine are not sufficiently immunogenic to raise an antibody titer to sufficient levels to provide protection against subsequent challenge, or to maintain the potential for mounting these levels over extended time periods. Another problem is that the vaccine may be deficient in inducing cell-mediated immunity which is a primary immune defense against bacterial and viral infection. Still another problem is that an individual patient might be immunosuppressed.

To obtain a stronger humoral and/or cellular response, it is common to administer a vaccine in a formulation containing an adjuvant. An adjuvant is a substance that enhances, nonspecifically, the immune response to an antigen, or which causes an individual to respond to an antigen who would otherwise without the adjuvant not respond to the antigen. An adjuvant is usually administered with an antigen, but may also be given before or after antigen administration. Suitable adjuvants for the vaccination of mammals include but are not limited to Adjuvant 65 (containing peanut oil, mannide monooleate and aluminum monostearate); Freund's complete or incomplete adjuvant; mineral gels such as aluminum hydroxide, aluminum phosphate and alum; surfactants such as hexadecylamine, octadecylamine, lysolecithin, dimethyldioctadecyl-ammonium bromide, N,N-dioctadecyl-N',N'-bis(2-hydroxymethyl) propanediamine, methoxyhexadecylglycerol and pluronic polyols; polyanions such as pyran, dextran sulfate, poly IC, polyacrylic acid and carbopol; peptides such as muramyl dipeptide, dimethylglycine and tuftsin; and oil emulsions. The antigens could also be administered following incorporation into liposomes or other microcarriers.

SUMMARY OF THE INVENTION

It has been surprisingly discovered that granulocyte-macrophage-colony stimulating factor (GM-CSF) is an effective vaccine adjuvant.

Accordingly, the present invention provides a method for enhancing the immune response of a mammal to a vaccine comprising administering to a mammal in need of vaccination an effective amount of GM-CSF in conjunction with a vaccine.

Preferably, the mammals treated will be humans and the GM-CSF utilized will be one of the human allotypes. Preferably, the GM-CSF will be administered from 1 to 14 days prior to or after the administration of the vaccine in an amount of about 0.1 to 100 micrograms (µg) per kilogram of body weight.

The present invention further provides for a pharmaceutical composition comprising an effective amount of GM-CSF, a natural, synthetic or recombinant antigen, and a pharmaceutically acceptable carrier.

Also claimed is a kit for enhancing an immunogenic response of a mammal to antigens in a vaccine comprising a first container having a pharmaceutical composition of GM-CSF contained therein; and a second container having a pharmaceutical composition of a vaccine contained therein.

DETAILED DESCRIPTION OF THE INVENTION

The teachings of the references cited in the present application are incorporated herein in their entirety by reference.

According to the present invention, we have surprisingly found that the immune response in a mammal, especially a human, to a vaccine can be effectively enhanced by the administration of an effective amount of GM-CSF in conjunction with the vaccine. The term "in conjunction with" as used herein refers to the administration of GM-CSF concurrently, before or following administration of a vaccine.

As used herein, "GM-CSF" means a protein which (a) has an amino acid sequence that is substantially identical to the sequence of mature (i.e., lacking a signal peptide) human GM-CSF described by Lee et al. *Proc. Natl. Acad. Sci. U.S.A.* 82: 4360 (1985) and (b) has biological activity that is common to native GM-CSF.

Substantial identity of amino acid sequences means that the sequences are identical or differ by one or more amino acid alterations (deletions, additions, substitutions) that do not substantially impair biological activity. Among the human GM-CSFs, nucleotide sequence and amino add heterogeneity have been observed. For example, both threonine and isoleucine have been observed at position 100 of human GM-CSF with respect to the N-terminal position of the amino acid sequence. Also, Schrimsher et al. [Biochem. J 247:195 (1987)] have disclosed a human GM-CSF variant in which the methionine residue at position 80 has been replaced by an isoleucine residue. GM-CSF of other species such as mice and gibbons (which contain only 3 methionines) and rats are also contemplated by this invention. Recombinant GM-CSFs produced in prokaryotic expression systems may also contain an additional N-terminal methionine residue, as is well known in the art. Any GM-CSF meeting the substantial identity requirement is included, whether glycosylated (i.e., from natural sources or from a eukaryotic expression system) or unglycosylated (i.e., from a prokaryotic expression system or chemical synthesis).

GM-CSF for use in this invention can be obtained from natural sources (U.S. Pat. No. 4,438,032; Gasson et al., supra; Burgess et al., supra; Sparrow et al., Wu et al., supra).

GM-CSF having substantially the same amino acid sequence and the activity of naturally occurring GM-CSF may be employed in the present invention. Complementary DNAs (cDNAs) for GM-CSF have been cloned and sequenced by a number of laboratories, e.g. Gough et al, *Nature*, 309:763 (1984) (mouse); Lee et al., *Proc. Natl. Acad. Sci. USA*, 82:4360 (1985) (human); Wong et al., *Science*, 228:810 (1985) (human and gibbon); Cantrell et al., *Proc. Natl. Acad. Sci. USA*, 82 :6250 (1985) (human), Gough et al., *Nature*, 309:763 (1984) (mouse); Wong et al., *Science*, 228:810 (1985) (human and gibbon); Cantrell et al., *Proc. Natl. Acad. Sci. U.S.A.*, 82:6250 (1985) (human).

GM-CSF can also be obtained from Immunex, Inc. of Seattle, Wash. and Schering-Plough Corporation of Kenilworth, N.J. and from Genzyme Corporation of Boston, Mass.

Adjuvant activity is manifested by a significant increase in immune-mediated protection by development of an immune response in an individual who otherwise would not respond at all to a vaccine. Enhancement of humoral immunity is typically manifested by a significant increase in the titer of antibody raised to the antigen.

The methods of the present invention to provide administration of GM-CSF in conjunction with a vaccine has the following advantages. The total antigenic load of vaccine to be administered may be reduced since less antigen in the presence of GM-CSF would elicit an immunologic response at least equivalent to that achieved by the administration of the normal amount of the vaccine. Since less antigen would be required per vaccination by administering GM-CSF in accordance with the present invention, the probability of undesirable side-effects associated with some vaccines currently in use would be reduced.

The immune response of certain types of individuals who respond poorly to vaccination would be enhanced by administering GM-CSF in conjunction with a vaccine. Types of individual who should benefit from the methods of the present invention include (1) those types having impaired immune responsiveness, (2) those individuals who appear normal but who are nevertheless nonresponsive to certain vaccines as well as (3) individuals undergoing immunosuppressive therapies such as radiation and chemotherapy.

Thus, we have discovered an effective method for (1) enhancing an effective primary immune response in mammals to antigens present in a vaccine, (2) enhancing an effective level of antibodies in mammals exposed to antigen in vaccines, and (3) enhancing a primary immune response in mammals to antigens present in a vaccine wherein the immune response by the mammal without the administration GM-CSF would not be strong enough or fast enough to prevent disease.

The vaccines contemplated for use in accordance with the present invention include but are not limited to bacterial vaccines, toxoid vaccines (inactivated toxins) and viral vaccines or mixtures thereof used for active immunization. See for example chapter 75 entitled "Immunizing Agents" in Remington's Pharmaceutical Sciences 14th Edition 1990 Mack Publishing Co. p 1426–1441 and the antitoxins, toxoids, vaccines and live vaccines approved by the U.S. Food and Drug Administration and listed on page 208–209 (Product Category Index) of the Physician's Desk Reference, 46th Ed. 1992. Suitable bacterial vaccines include bacterial vaccines against the following disease entities or states: cholera, pertussis, plague, typhoid fever, meningitis, pneumococcal pneumonia, *H. influenzae* type B, leprosy, gonorrhea, Group B meningococcus, and Group B streptococcus, Gram-negative sepsis, *E. coli* sepsis, and *Pseudomonas aeruginosa*. Suitable toxoids include diphtheria toxoid, botulism toxid, and tetanus toxoid. Suitable vital vaccines include live and inactivated viral vaccines against the following disease entities or states: poliomyelitis, measles rubella, yellow fever, mumps, hepatitis B, hepatitis C and viral influenza.

The suitable "multiple antigens" include diphtheria and tetanus toxoids, the triple antigen-diphtheria, pertussis and tetanus toxoids such as are available from Connaught Laboratories, Inc. Swiftevater, Pa. 18370. The wide variety of viral strains and cell substrates and the the varied immunization schedules used in different countries are disclosed in White, D.O., and Fenner F., *Medical Virology.* 3rd Edition (Academic Press 1986).

In addition, the GM-CSF will typically be used to enhance the protection afforded by animal or human vaccines that are considered "weak" (i.e., provide diminished protection in terms of level, extent, and/or duration). Examples of such vaccines are bacterins such as Bordetella bacterin, *Escherichia coli* bacterins, Haemophilus bacterins, Leptospirosis vaccines, *Moraxella bovis* bacterin, Pasteurella bacterin and *Vibrio fetus* bacterin, pneumococcal vaccines and attenuated live or killed virus products or recombinant antigenic viral products such as hepatitis B, influenza A & B, bovine respiratory disease vaccine, infectious bovine rhinotracheitis, parainfluenza-3, respiratory syncytial virus, bovine virus diarrhea vaccine, equine influenza vaccine, feline leukemia vaccine, feline respiratory disease vaccine rhinotracheitiscalicipneumonitis viruses, canine parovovirus vaccine, transmissible gastroenteritis vaccine, pseudorabies vaccine, and rabies vaccine.

The term "effective amount" as used herein regarding the effective amount of GM-CSF administered in accordance with the present invention means an amount of GM-CSF which produces an increase in antibody level sufficient to provide increased protection from an infectious agent than if a vaccine had been administered without GM-CSF. However, it should be noted a significant increase in antibody level may be relatively small. The effective amount of GM-CSF administered is from 0.1 to 500 μg of GM-CSF per kilogram of body weight. More preferably, the effective amount administered is from 1 μg to 100 μg and most preferably from 5 to 50 μg of GM-CSF per kilogram of body weight.

The amount, frequency and period of administration will vary depending upon factors such as the level of the specific antibody titers, the class of antibody to be induced, the vaccine type as well as the age of the patient and general physical condition. The GM-CSF can be 5 administered before, concurrently with or after the vaccine is administered. Preferably, one dose of GM-CSF is given to the patient from 1 to 14 days prior to the administration of the vaccine. Most preferably the GM-CSF is administered about 24 hours prior to or after the administration of the vaccine.

The GM-CSF will normally be administered separately from the vaccine, although it may be administered in combination with the vaccine. When GM-CSF is combined with the vaccine, the composition administered contains an immunogen that is effective in eliciting a specific response to a given pathogen or antigen, a pharmaceutically acceptable vaccine carrier and an immunopotentiating amount of GM-CSF. Administration of GM-CSF can be subcutaneous, intravenous, parenteral, intramuscular, or any other acceptable method. Preferably, GM-CSF is administered prior to the administration of the vaccine and at the same site where the vaccine is to be administered. The formulations and pharmaceutical compositions contemplated by the above dosage forms can be prepared with conventional pharmaceutically acceptable excipients and additives, using conventional techniques. Other adjuvants may be administered either with the vaccine or together with the GM-CSF.

If multiple doses of the vaccine are to be administered over a period of time, additional GM-CSF may be administered in conjunction with each subsequent dose of the vaccine. The amount of GM-CSF which is administered with each subsequent dose of the vaccine may be more, the same or less than the amount of GM-CSF administered in conjunction with the initial dose of the vaccine. The amount of GM-CSF administered with each subsequent dose of the vaccine will depend upon the antibody response of the patient after the first dose of the vaccine.

Solutions of GM-CSF to be administered may be reconstituted from lyophilized powders and they may additionally contain preservatives buffers, dispersants, etc. Preferably, GM-CSF is reconstituted with any isotonic medium normally utilized for subcutaneous injection, e.g., preservative-free sterile water.

A sustained release formulation of GM-CSF can be administered which will result in a longer serum half-life of the drug. Examples of such formulations are the following:

| Formulation 1 | |
|---|---|
| INGREDIENTS | |
| Lyophilized GM-CSF | 10–1000 mcg |
| Zinc Acetate | 4.0 mg |
| Protamine Sulfate | 2.5 mg |
| Sodium Hydroxide | 0.6 mg |
| Water for Injection q.s. | 1 ml |

To prepare the sustained release preparation of GM-CSF according to Formulation 1, the lyophilized GM-CSF is dissolved in a portion of the Water for Injection and the pH of the solution is adjusted to 8.2 using sodium hydroxide. The protamine sulfate is added and the mixture is agitated, after which the zinc acetate is added and the mixture is again agitated. The total solution is brought to the final volume with the remaining Water for Injection. Preferably, the sodium hydroxide, protamine sulfate and zinc acetate are added as concentrated aqueous solutions (e.g. for protamine, 100 microliters of a 25 mg/ml aqueous solution).

| Formulation 2 | |
|---|---|
| INGREDIENTS | |
| Lyophilized GM-CSF | 10–1000 mcg |
| Water-for-injection for reconstitution | 0.2 ml |
| Dioctyl Sodium Sulfosuccinate | 1 mg |
| Peanut oil for emulsion | 2 ml |
| Peanut oil for gel | 2 ml |
| Aluminum monostearate | 50 mg |

To prepare the sustained release preparation of GM-CSF according to Formulation 2, the aluminum monostearate is mixed into the peanut oil for the gel and heat elevated to form the gel according to known methods.

The dioctyl sodium sulfosuccinate is dissolved into the Water for Injection. The lyophilized GM-CSF is reconstituted with the dioctyl sodium sulfosuccinate solution, the resultant solution is transferred into the peanut oil for emulsion and mixed by vortexing. The resultant emulsion is then mixed into the previously prepared gelled peanut oil and mixed by vortexing.

| Formulation 3 | |
|---|---|
| INGREDIENTS | |
| Lyophilized GM-CSF | 10–1000 mcg |
| Copper Acetate | 0.2 mg |
| Sodium Phosphate, Dibasic | 2.27 mg |
| Sodium Phosphate, Monobasic | 0.55 mg |
| Sodium Hydroxide | 0.6 mg |
| Water for Injection q.s. | 1 ml |

To prepare the sustained release preparation of GM-CSF according to Formulation 3, the monobasic and dibasic sodium phosphates are dissolved in a portion of the Water for Injection. The lyophilized GM-CSF is then dissolved in this solution and the pH is adjusted to 7.8 with the sodium hydroxide. The copper acetate is then added and the solution is agitated. The solution is brought to final volume using the remaining Water for Injection. Preferably, the sodium hydroxide and copper acetate are added as concentrated aqueous solutions (e.g., for copper acetate, 100 microliters of a 2 mg/ml aqueous solution).

Additional Sustained Release Formulations

Additional sustained release formulations of GM-CSF can be prepared using micoencapsulated or microspheres of GM-CSF prepared using polymers such as polyanhydrides, polyphosphazenes, collagen, alginates, poly(methacrylates), gelatin, poly(hydroxybutyrate), poly(caprolactone), ethylene vinyl acetate or polylactide glycolide.

Sustained release GM-CSF can also be prepared as chemical conjugates of GM-CSF using polyethylene glycol, dextran poly(aminoacids) and other similar polymers.

The effect of GM-CSF on enhancing the immune response of a vaccine is illustrated by the following non-limiting human clinical data which should not be construed to limit the scope of the disclosure.

EXAMPLE 1

Recombinant human GM-CSF was shown to enhance the efficacy of recombinant hepatitis B vaccine on dialysis patients who had not responded to the hepatitis B vaccine.

The objective of the present experiment was to determine whether the co-administration of GM-CSF and hepatitis vaccine would be capable of restoring immunologic responsiveness to patients with renal failure who had been previously unresponsive to hepatitis vaccination.

Fifteen dialysis patients who had not responded to at least 3 attempts at vaccination with hepatitis B vaccine as determined by their antibody titers against the hepatitis B surface antigen (HBsAg) were treated with GM-CSF. Six patients were injected subcutaneously with 0.5 micrograms (µg) of GM-CSF per kilogram (kg) weight of the patient, (produced in an E. coli. expression system by Scher/ng-Plough, Kenilworth, N.J., USA), five patients with 5 µg of GM-CSF per kg weight of the patient and four patients with 10 µg of GM-CSF per kg weight of the patient, and the site of injection was marked. Twenty-four hours after administration of the GM-CSF, the patients were each administered 40 µg of the hepatitis B vaccine, HBVax® (Merck, Sharpe and Dohme, Gmbh, Darmstadt, Federal Republic of Germany) at the same site as the GM-CSF was injected. Four weeks after administration of the vaccine, blood samples were drawn from the patients and the samples were tested for the presence of anti-hepatitis B antibody. The results are shown in the table below.

TABLE 1

| Dosage of GM-CSF (μg/kg wt.) | Antibody titer against HBsAg Units*/liter |
|---|---|
| 0.5 | 0 |
| 0.5 | 0 |
| 0.5 | 0 |
| 0.5 | 0 |
| 0.5 | 0 |
| 0.5 | 710 |
| 5.0 | 0 |
| 5.0 | 35 |
| 5.0 | 125 |
| 5.0 | 920 |
| 5.0 | 2600 |
| 10.0 | 0 |
| 10.0 | 0 |
| 10.0 | 440 |
| 10.0 | 7240 |

*A unit is defined as the reciprocal of the serum dilution which produced a half maximal response in a standard ELISA.

As can be seen the data presented above, GM-CSF was an effective adjuvant used in conjunction with the hepatitis B vaccine.

EXAMPLE 2

Recombinant human GM-CSF was shown to enhance the efficacy of viral influenza vaccine in elderly patients.

Human influenza viruses, occurring during pandemics (Influenza A) and epidemics (Influenza A and B), cause significant excess morbidity and morality in the elderly, not only in those with underlying chronic diseases, but also in apparently healthy subjects. Since influenza vaccine has been shown to provide benefits in reducing both morbidity and mortality, flu vaccine is strongly recommended in subjects at high risk to develop flu related complications, and substantial resources are expended annually in an effort to vaccinate high-risk subjects.

However, despite large immunization programs, influenza remains a significant cause of illness and death in the elderly. Several methods, such as administering two to three times the standard vaccine dose or giving a booster dose one month after a first standard dose have not been shown to improve immunoresponse to flu vaccine in the elderly.

Accordingly, a double-blind, placebo-controlled, dose escalation study was carried out to determine whether the immunoresponse to flu vaccine is enhanced by the administration of recombinant GM-CSF. Five different dosages of recombinant GM-CSF (produced in an *E. coli* expression system by Schering-Plough, Kenilworth, N.J., USA) were tested, namely, 0.25, 0.5, 1, 2.5 and 5 μg/kg in comparison to placebo. Sixty elderly healthy subjects were enrolled. They received recombinant GM-CSF or a placebo subcutaneously in one arm just before the intramuscular administration of the French 1992–1993 trivalent flu vaccine (A/Singapore/6/86 [H1N1], A/Beijing/353/89 [H3N2] and B/Yamagata/16/88) in the other arm (Pasteur Vaccins, Marnes-la-Coquette, France). Specific hemoagglutinin-inhibiting (HAI) antibody titers against the three flu virus strains were determined at baseline and 1, 3 and 6 weeks after vaccination. None of the 15 patients who received placebo with the flu vaccine showed simultaneous seroconversion to all the three strains of the flu vaccine, whereas 5 (56%) and 3(33%) of the 9 patients receiving 2.5 and 5 μg/kg of recombinant GM-CSF seroconverted to all three strains.

The protocol which was used is described in more detail below.

Materials and Methods

Subject Selection. Subjects were healthy elderly people of both sexes and of at least 65 years of age. Volunteers were screened by medical history, and laboratory tests that included a complete blood cell count, biochemistry, urinalysis and serology. Subjects had to have a baseline hemoagglutinin-inhibiting (HAI) antibody titers ≤1:40 for the A-H1N1 and B influenza strains and ≤1:80 for the A-H3N2 influenza strain contained in the 1992–1993 French flu vaccine. Subjects with history of severe or unstable chronic illness or malignancy, taking antineoplastic or immunosuppressive drugs, with significantly abnormal results of the screening laboratory tests, allergic to eggs, with history of an influenza like illness in the past six months, or acutely ill at the time of specimen collection were excluded from the study.

Study Design. The study was designed as a double-blind, placebo-controlled, dose finding study.

Drug administration and vaccination. The 60 subjects enrolled in the study were divided into five dose groups of 12 subjects each. Each group received a single dose of 0.25, 0.5, 1, 2.5 or 5 μg/kg of r GM-CSF or placebo. Recombinant GM-CSF or placebo were administered subcutaneously in the deltoid area of the right arm, immediately after which all the subjects received 0.5 ml of a licensed 1992–1993 trivalent subvirion vaccine that contained 15 μg each of HAs from A/Singapore/6/86 (H1N1), A/Beijing/353/89 (H3N2) and B/Yamagata/16/88 viruses (Pasteur Vaccins, Marnes-la-Coquette, France) intramuscularly in the deltoid of the left arm.

Specimen collection. Blood serum and throat swabs for the virological cultures were obtained from each subject before the start of the study and 1,3 and 6 weeks after vaccination.

Serum antibodies. HAI antibodies to influenza A/Singapore (NH1N1), A/Beijing (H3N2) and B/Yamagata virus antigens were measured in serum specimens by a standard hemo-agglutination inhibition assay. Results for the preliminary analysis of the sera collected until Week 6 were obtained by testing all specimens on the same day using identical reagents. The initial starting dilution was 1:20. HAI antibody titers less than 1:20 were defined as "Not detectable" titers.

Statistical analysis. Success according to the antibody titers were defined in two different ways:

Seroconversion: a four-fold increase of the HAI antibody titers over baseline at Week 6.

Seroprotection: HAI antibody titers greater than baseline and at least equal to 1:40 at Week 6.

The number of successes based on these definitions were analyzed using the Fisher's exact tests. The placebo groups of the different dose groups were pooled together.

Results

Subject characteristics. All the 60 healthy elderly volunteers enrolled in the study completed the assessment at the 6th week. Table 3 reports HAI antibody titers at baseline. Most of the subjects had baseline HAI antibody titers below protective levels, that is below 1:40. Distribution of the baseline titers was similar among all treatment groups, with the exception of the group treated with 0.5 μg/kg in which most of the patients had no detectable antibody titers.

Immunoresponse. Table 4 shows the number of patients who seroconverted to all three strains 6 weeks after the administration of GM-CSF/placebo and flu vaccine. Results are also reported separately for each strain.

None of the 15 subjects who received placebo with the flu vaccine showed simultaneous seroconversion to all three flu virus strains, whereas 5 of 9 (56%) and 3 of 9 (33%) of the subjects treated with 2.5 and 5 µg/kg of the rGM-CSF were seroconverted to all three strains. In addition, when the results are examined separately for each flu strain, seroconversion rates for 2.5 and 5 µg/kg of rGM-CSF are consistently higher (ranging from 44% to 67%) than those observed with placebo (ranging from 13% to 20%). Interestingly, seroconversion rates observed with the lowest dose (0.25 µg/kg) have been higher than those observed with 0.5 and 1 µg/kg.

As shown in Table 5, the conclusion of the results do not change also using "seroprotection" as definition of success. As expected, seroprotection rates are higher than those of seroconversion in all treatment groups, because seroprotection is easier to accomplish than seroconversion. Again, patients treated with rGM-CSF showed a higher immuno-response rate to the flu vaccine than those treated with placebo. In fact, 5 of 9 (56%) and 3 of 9 (33%) patients treated with 2.5 and 5 µg/kg were protected against all three strains, whereas only 1 of the 15 subjects (7%) treated with placebo was seroprotected against all three strains.

TABLE 2

Study design.

| | Number of subjects | |
|---|---|---|
| | CSF 39300 | Placebo |
| Group I: 0.25 µg/kg | 9 | 3 |
| Group II: 0.5 µg/kg | 9 | 3 |
| Group III: 1. µg/kg | 9 | 3 |
| Group IV: 2.5 µg/kg | 9 | 3 |
| Group V: 5. µg/kg | 9 | 3 |

TABLE 3

HAI antibody titers at baseline. The table reports the number of subjects in each treatment group according to baseline HAI antibody titers for each of the three flu strains.

| | Number of subjects with specific HAI antibody titers at baseline | | | | | | | | | |
|---|---|---|---|---|---|---|---|---|---|---|
| | A/Beijing [H3N2] | | | | A/Singapore [H1N1] | | | B/Yamagata | | |
| Baseline HAI antibody titers: | <1:20 | 1:20 | 1:40 | 1:80 | <1:20 | 1:20 | 1:40 | <1:20 | 1:20 | 1:40 |
| Placebo + flu vaccine | 5 | 6 | 4 | — | 10 | 4 | 1 | 10 | 2 | 3 |
| CSF 39300 + flu vaccine | | | | | | | | | | |
| 0.25 µg/kg | 4 | 3 | 2 | — | 6 | 1 | 2 | 5 | 4 | — |
| 0.5 µg/kg | 1 | 5 | 3 | — | 7 | 1 | 1 | 4 | 1 | 4 |
| 1 µg/kg | 2 | 4 | 3 | — | 4 | 3 | 2 | 4 | 2 | 3 |
| 2.5 µg/kg | 2 | 4 | 1 | 2 | 6 | 2 | 1 | 4 | 5 | — |
| 5 µg/kg | 9 | — | — | — | 8 | 1 | — | 8 | 1 | — |

TABLE 4

Results of seroconverstion.

Seroconversion is defined as a four-fold increase of the HAI antibody titers over baseline. The second column of the table reports the number of subjects who seroconverted to all three strains contained in the flu vaccine. The last three columns show the number of seroconversion observed for each flu strain.

| | Patients simultaneously seroconverted to all three strains | Number of seroconversion observed for the diferent flu strains | | |
|---|---|---|---|---|
| | | A/Beijing [H3N2] | A/Singapore [H1N1] | B/Yamagata |
| Placebo + flu vaccine | 0/15 (0%) | 3/15 (20%) | 3/15 (20%) | 2/15 (13%) |
| CSF 39300 + flu vaccine | | | | |
| 0.25 µg/kg | 2/9 (22%) | 4/9 (44%) | 4/9 (44%) | 3/9 (33%) |
| 0.5 µg/kg | 0/9 (0%) | 2/9 (22%) | 3/9 (33%) | 1/9 (11%) |
| 1 µg/kg | 1/9 (11%) | 2/9 (22%) | 1/9 (11%) | 4/9 (44%) |
| 2.5 µg/kg | 5/9 (56%) | 6/9 (67%) | 5/9 (56%) | 5/9 (56%) |
| 5 µg/kg | 3/9 (33%) | 4/9 (44%) | 4/9 (44%) | 5/9 (56%) |

TABLE 5

Results of seroprotection. Seroprotection is defined as an increase of the HAI antibody titers over baseline and at least 1:40. The second column of the table reports the number of subjects who develop seroprotective HAI antibody titers against all three strains contained in the flu vaccine. The last three columns show the number of seroprotection observed for each flu strain.

| | Patients simultaneously seroprotected to all three strains | Number of seroprotection observed for the different flu strains | | |
|---|---|---|---|---|
| | | A/Beijing [H3N2] | A/Singapore [H1N1] | B/Yamagata |
| Placebo + flu vaccine | 1/15 (7%) | 8/15 (53%) | 5/15 (33%) | 3/15 (20%) |
| CSF 39300 + flu vaccine | | | | |
| 0.25 µg/kg | 4/9 (44%) | 6/9 (67%) | 5/9 (56%) | 6/9 (67%) |
| 0.5 µg/kg | 1/9 (11%) | 5/9 (56%) | 3/9 (33%) | 3/9 (33%) |
| 1 µg/kg | 2/9 (22%) | 4/9 (44%) | 3/9 (33%) | 4/9 (44%) |
| 2.5 µg/kg | 5/9 (56%) | 8/9 (89%) | 5/9 (56%) | 6/9 (67%) |
| 5 µg/kg | 3/9 (33%) | 4/9 (44%) | 4/9 (44%) | 5/9 (56%) |

What is claimed is:

1. A method for enhancing an immune response of a mammal to a vaccine comprising administering to a mammal in need of vaccination an effective amount of granulocyte-macrophage-colony stimulating factor (GM-CSF) in conjunction with a vaccine, said effective amount of GM-CSF being sufficient to enhance an immune response to said vaccine.

2. The method of claim 1 wherein the vaccine is selected from a group consisting of hepatitis B vaccine and influenza vaccine.

3. The method of claim 1 wherein the GM-CSF which is administered is contained within a sustained release formulation.

4. The method of claim 1 wherein the immune response is an antibody-mediated immune response.

5. The method of claim 1 wherein said mammal is a human.

6. The method of claim 4 wherein said mammal is a human.

7. A pharmaceutical composition comprising an effective amount of GM-CSF and a vaccine, said effective amount of GM-CSF being sufficient to enhance an immune response to said vaccine.

8. The pharmaceutical composition of claim 7 wherein the GM-CSF is contained within a sustained release formulation.

9. A kit for enhancing an immunogenic response of a mammal to antigens in a vaccine comprising a container of a pharmaceutical composition of GM-CSF and a pharmaceutically acceptable carrier therefor; and a container of a pharmaceutical composition of a vaccine and a pharmaceutically acceptable carrier therefor.

10. The kit of claim 9 wherein the GM-CSF is contained within a sustained release formulation.

* * * * *